(12) United States Patent
Farber et al.

(10) Patent No.: US 12,194,295 B2
(45) Date of Patent: Jan. 14, 2025

(54) METHOD AND APPARATUS FOR DELIVERING TUMOR TREATING FIELDS TO A TORSO, AND METHOD FOR DETERMINING LOCATIONS FOR TRANSDUCERS TO DELIVER TUMOR TREATING FIELDS

(71) Applicant: Novocure GmbH, Root (CH)

(72) Inventors: Ori Farber, Haifa (IL); Ariel Naveh, Haifa (IL); Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 481 days.

(21) Appl. No.: 17/487,432

(22) Filed: Sep. 28, 2021

(65) Prior Publication Data

US 2022/0096829 A1    Mar. 31, 2022

Related U.S. Application Data

(60) Provisional application No. 63/181,031, filed on Apr. 28, 2021, provisional application No. 63/085,934, filed on Sep. 30, 2020.

(51) Int. Cl.
| | |
|---|---|
| *A61N 1/36* | (2006.01) |
| *A61B 34/10* | (2016.01) |
| *A61N 1/04* | (2006.01) |
| *A61N 1/06* | (2006.01) |
| *G16H 20/30* | (2018.01) |

(Continued)

(52) U.S. Cl.
CPC ......... *A61N 1/36002* (2017.08); *G16H 20/40* (2018.01); *A61N 1/0476* (2013.01)

(58) Field of Classification Search
CPC .. A61N 1/36002; A61N 1/0476; A61N 1/403; A61N 1/40; A61N 1/3603; A61N 1/0456; A61N 1/0492; A61N 1/06; G16H 20/40; G16H 20/30; G16H 50/50; A61B 2034/104; A61B 2034/105
See application file for complete search history.

(56) References Cited

U.S. PATENT DOCUMENTS

| | | |
|---|---|---|
| 7,565,205 B2 | 7/2009 | Palti |
| 2005/0187581 A1* | 8/2005 | Hara ...................... A61N 1/326 607/2 |

(Continued)

OTHER PUBLICATIONS

Miklos Pless et al.; "A phase 1/11 trial of Tumor Treating Fields (TTFields) therapy in combination with pemetrexed for advanced non-small cell lung cancer;" Lung Cancer 81 (2013) 445-450 (Year: 2013).*

(Continued)

*Primary Examiner* — Lynsey C Eiseman
*Assistant Examiner* — Christopher J Mutchler
(74) *Attorney, Agent, or Firm* — McCarter & English, LLP; Michael A. Sartori

(57) ABSTRACT

A method of applying tumor treating fields to a torso of a subject's body, the method including: locating a first transducer at a first location of the subject's body, the first location being on the torso of the subject's body; locating a second transducer at a second location of the subject's body, the second location being below the torso of the subject's body; and inducing an electric field between at least part of the first transducer and at least part of the second transducer.

9 Claims, 12 Drawing Sheets

(51) Int. Cl.
　　　*G16H 20/40*　　　(2018.01)
　　　*G16H 50/50*　　　(2018.01)

(56) References Cited

U.S. PATENT DOCUMENTS

| | | |
|---|---|---|
| 2017/0014637 A1 | 1/2017 | Basser |
| 2018/0001075 A1 | 1/2018 | Kirson et al. |
| 2018/0001078 A1* | 1/2018 | Kirson .................. A61N 1/321 |
| 2018/0050200 A1 | 2/2018 | Wasserman et al. |
| 2018/0085575 A1 | 3/2018 | Travers et al. |
| 2019/0117956 A1 | 4/2019 | Wenger et al. |
| 2020/0114141 A1 | 4/2020 | Bomzon et al. |
| 2020/0129761 A1 | 4/2020 | Bomzon et al. |
| 2020/0155835 A1 | 5/2020 | Wasserman et al. |
| 2021/0299439 A1 | 9/2021 | Shamir et al. |

OTHER PUBLICATIONS

Washington State Health Care Authority, Health Technology Assessment Program (HTA); "Novocure (Tumor Treating Fields) Updated Final Evidence Report;" Dec. 26, 2015 (Year: 2015).*

Wenger et al., "A Review on Tumor-Treating Fields (TTFields): Clinical Implications Inferred From Computational Modeling," IEEE Reviews in Biomedical Engineering, vol. 11, 2018, pp. 195-207.

* cited by examiner

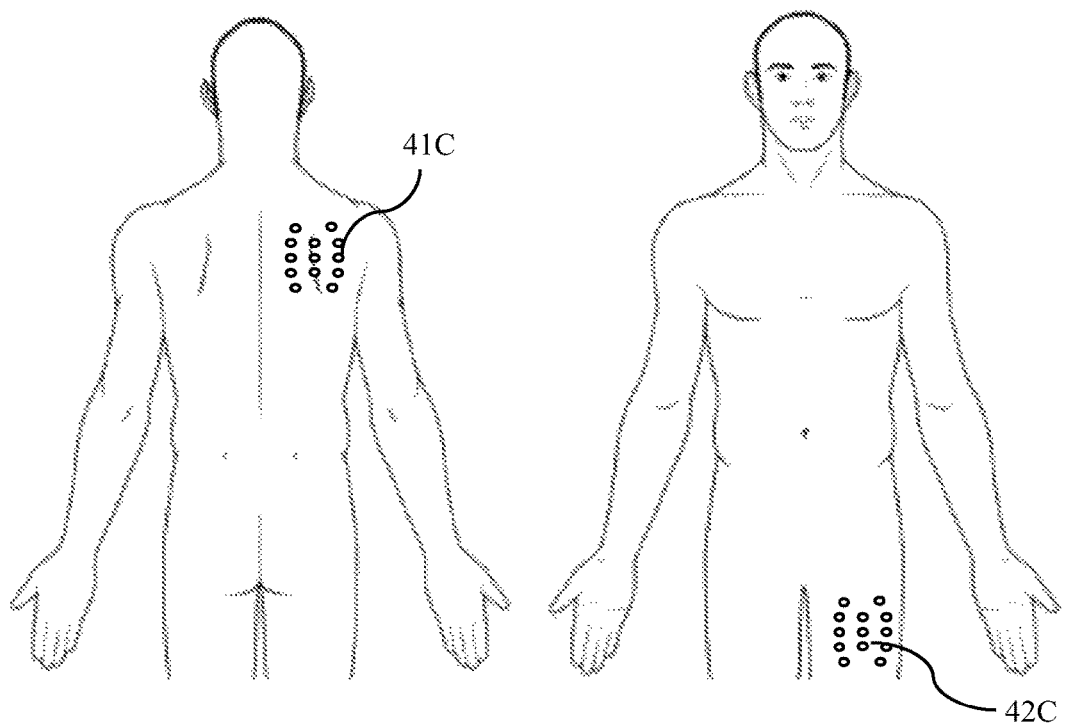
FIG. 4C
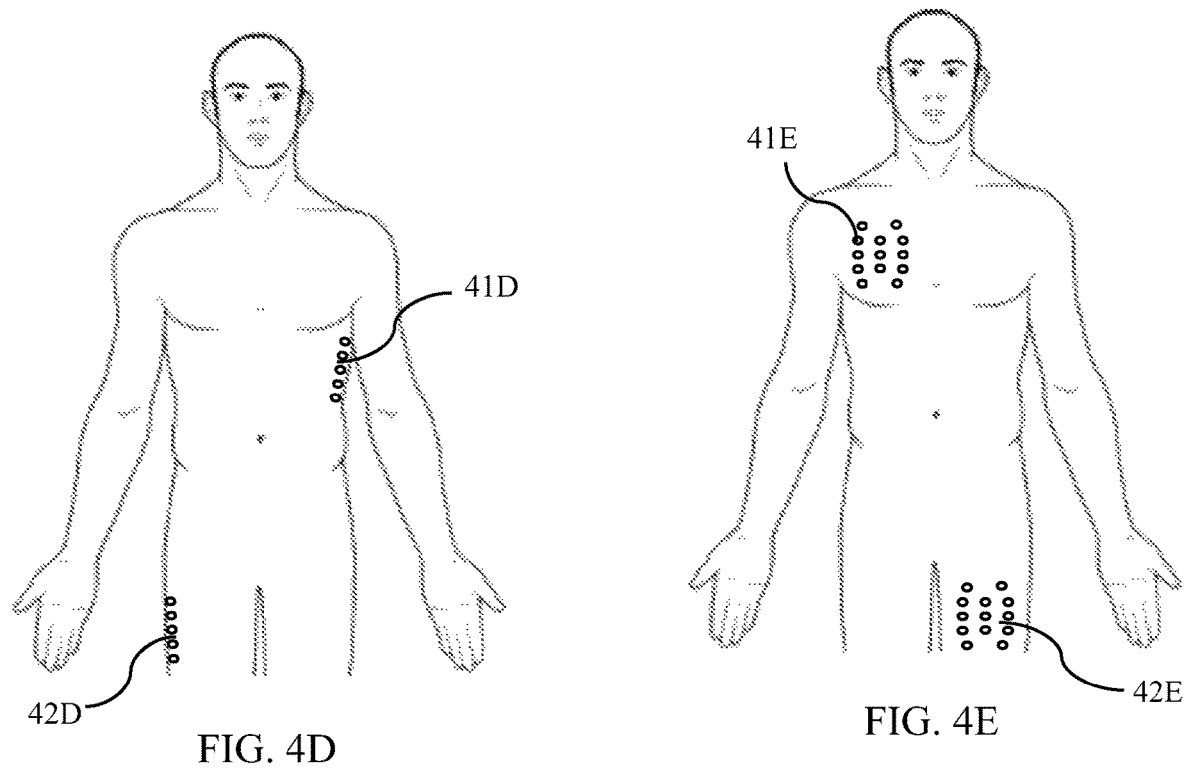
FIG. 4D
FIG. 4E

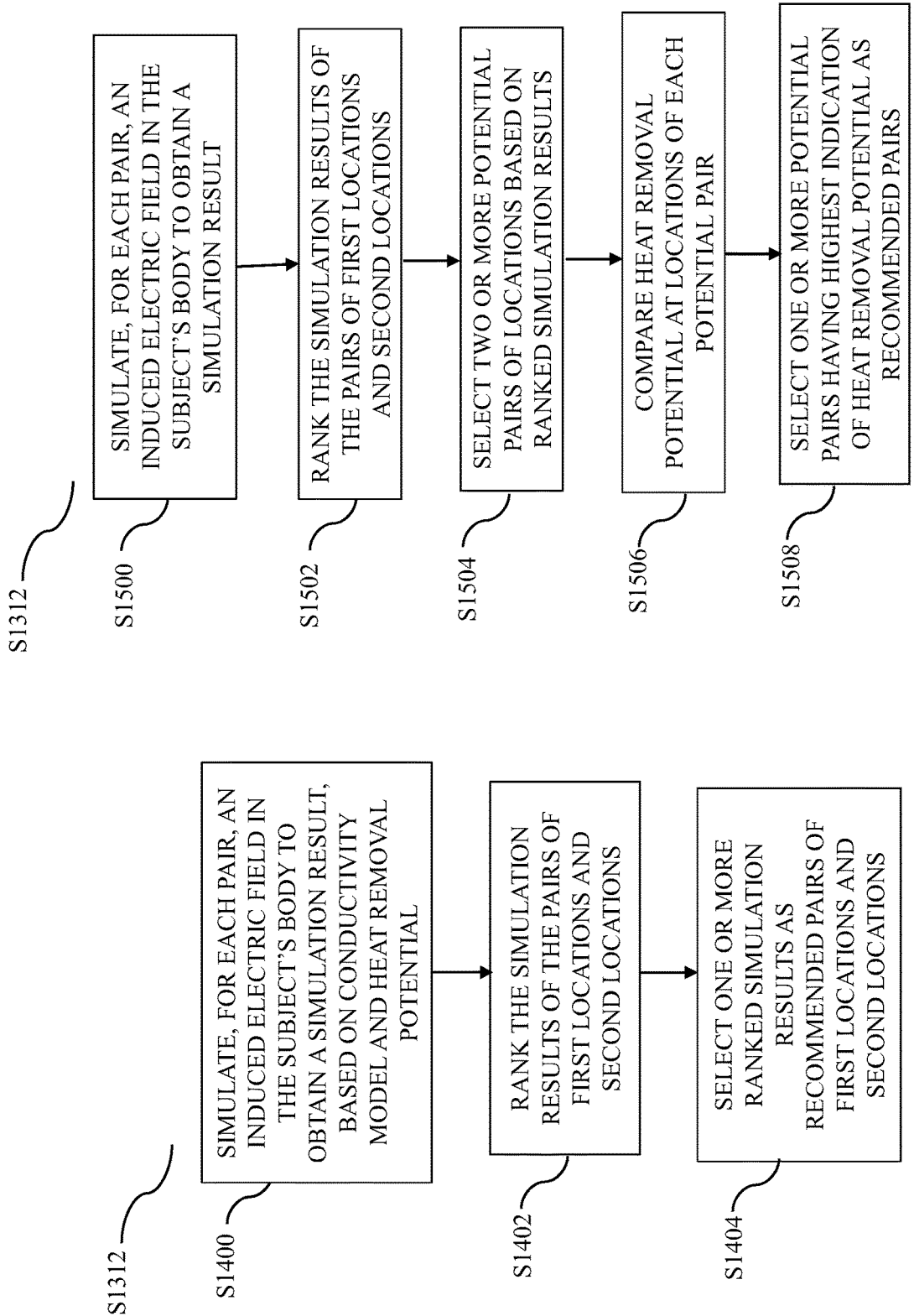

METHOD AND APPARATUS FOR DELIVERING TUMOR TREATING FIELDS TO A TORSO, AND METHOD FOR DETERMINING LOCATIONS FOR TRANSDUCERS TO DELIVER TUMOR TREATING FIELDS

CROSS-REFERENCE TO RELATED APPLICATIONS

This application claims priority to U.S. Patent Application No. 63/085,934 filed Sep. 30, 2020 and U.S. Patent Application No. 63/181,031 filed Apr. 28, 2021, both of which are incorporated herein by reference.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed on the patient's body and applying AC voltages between the transducers. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

SUMMARY OF THE INVENTION

One aspect of the invention is directed to a method of applying tumor treating fields to a torso of a subject's body. The method comprises: locating a first transducer at a first location of the subject's body, the first location being on the torso of the subject's body; locating a second transducer at a second location of the subject's body, the second location being below the torso of the subject's body; and inducing an electric field between at least part of the first transducer and at least part of the second transducer.

The above aspect of the invention is exemplary, and other aspects and variations of the invention will be apparent from the following detailed description of embodiments.

BRIEF DESCRIPTION OF THE DRAWINGS

FIGS. 4A-4E depict examples of transducer layouts with one pair of transducers.

FIG. 11 is a flowchart depicting using heat removal potential in a simulation.

FIG. 12 is a flowchart depicting using heat removal potential to rank simulation results.

DESCRIPTION OF EMBODIMENTS

This application describes exemplary methods and apparatuses to apply TTFields to a torso of a subject's body and may be used to treat one or more cancers located in the torso of the subject's body. The torso is the central part of the subject's body including the thorax and the abdomen. Many abdominal cancers may metastasize to the thorax area and vice versa. For this reason, it may be beneficial to deliver TTFields to the entire thorax and abdomen simultaneously. Pre-clinical experiments suggest that in order exert a therapeutic effect, TTField intensities should exceed a threshold of about 1 V/cm.

Figure 1:
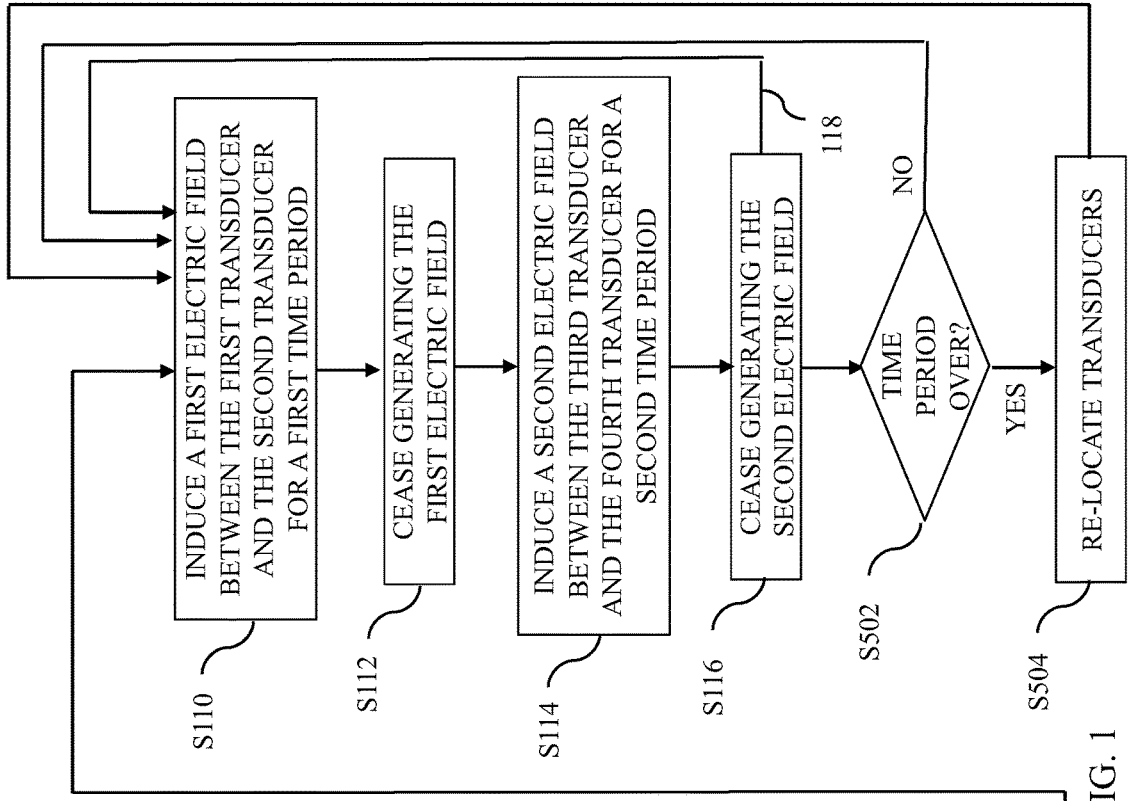
FIG. 1 is a flowchart depicting an example of applying TTFields to a torso.
Figure 1:
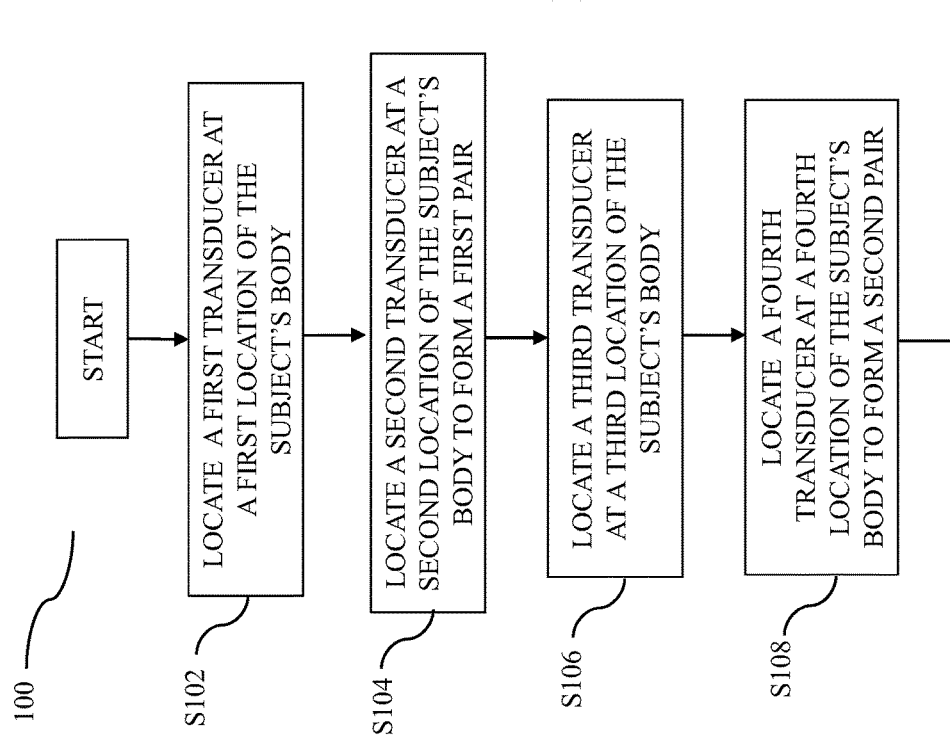

FIG. 1 describes an example method 100 of applying TTFields to the torso of a subject's body. With reference to FIG. 1, at step S102, the method 100 comprises locating a first transducer at a first location of the subject's body, wherein the first location is on the torso of the subject's body. At step S104, a second transducer is located at a second location of the subject's body, wherein the second location is below the torso of the subject's body. Below the torso of the subject's body may include, for example, on the thigh of the subject's body. The first and second transducers form the first pair of transducers. The first and second transducers are capacitively coupled. In another example, the transducers are not capacitively coupled.

At step S106, a third transducer is located at a third location of the subject's body, wherein the third location is on the torso of the subject's body and is not overlapping with the first location. At step S108, a fourth transducer is located at a fourth location of the subject's body, wherein the fourth location is below the torso of the subject's body and is not overlapping with the second location. The third and fourth transducers form the second pair of transducers. The third and fourth transducers are capacitively coupled. In another example, the transducers are not capacitively coupled. The transducers may be electric field generators. One or more of the first, second, third, and the fourth transducers may comprise an array, or grouping of electrode elements. Each array of electrode elements may comprise a plurality of ceramic disks, each disk being approximately 2 cm in diameter and approximately 1 mm in thickness. Each transducer may cover a surface area of approximately 140 to 250 $cm^2$.

At step S110, a first electric field is induced between the first transducer and the second transducer for a first time period. The first electric field is induced by applying a first AC voltage generated by an AC generator to the first pair of transducers and has, for example, a low intensity (e.g., 1-4 V/cm) and intermediate frequency range (e.g., 125-250 kHz, or in some cases, 50-500 kHz). The first AC voltage is applied to the first pair of transducers for the first time period (e.g., one second). At step S112, after the first time period, the generation of the first electric field is ceased. That is, the AC generator stops generating the first AC voltage.

At step S114, a second electric field is induced between the third transducer and the fourth transducer for a second time period. The second electric field is induced by applying a second AC voltage generated by the AC generator to the second pair of transducers. The second electric field may or may not have the same intensity and frequency as the first electric field. The second AC voltage is applied to the second pair of transducers for the second time period. The first time period and the second time period may be the same or different. At step S116, after the second time period, the generation of the second electric field is ceased. That is, the AC generator stops generating the second AC voltage. In some embodiments, after the second electric field is ceased, the process automatically repeats (arrow 118) in steps S110, S112, S114, and S116. The electric fields are induced in a thorax and an abdomen of the subject's body.

In other embodiments, the method 100 may further include changing the locations of the subject's body where the electric field is applied. This may help to mitigate the risk of skin irritation, thereby reducing any discomfort of the subject. The method 100 may include steps S502 and S504. At step S502, a third time period is checked. The third time period (which may be in hours or days) determines when the locations of the transducers should be changed. Once the third time period has ended, the locations of the transducers are moved to new locations on the subject's body. If the third time period is not over, flow proceeds to step S110. If the third time period is over, flow proceeds to step S504. At step S504, the transducers are re-located on the subject's body. The first transducer, the second transducer, the third transducer and the fourth transducer are re-located to a new first location, a new second location, a new third location, and a new fourth location of the subject's body. The new first, second, third, and fourth locations do not overlap with the previous first, second, third, and fourth locations, respectively. In alternative embodiments, the new locations may partially overlap with the previous locations. After the transducers are re-located at step S504, flow proceeds to step S110 and the flow repeats.

Figure 2:
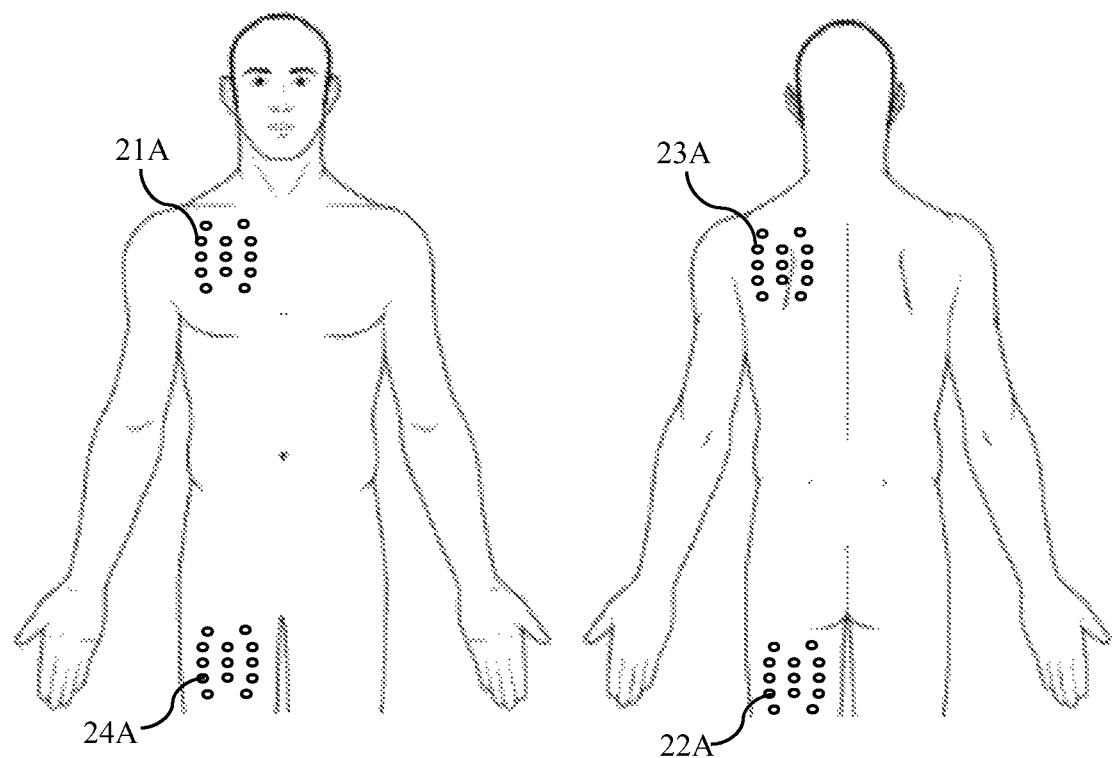
FIG. 2 depicts an example transducer layout for applying TTFields to the torso.

FIG. 2 depicts an example of a transducer layout for applying TTFields to a subject's body. FIG. 2 depicts one example of a transducer layout of two pairs of transducers with four transducers used for applying TTFields to the torso of the subject's body. In this example, the first transducer 21A and the third transducer 23A are located on the thorax of the subject's body, and the second transducer 22A and the fourth transducer 24A are located on the thighs of the subject's body. In one example, the first transducer 21A is located on the front of the thorax, the third transducer 23A is located on the back of the thorax, the second transducer 22A is located on a back or an outer side of the thighs, and the fourth transducer 24A is located on the front or inside of the thighs. In a more specific example, the first transducer 21A is located on the front of the right thorax; the third transducer 23A is located on the back of the left thorax; the second transducer 22A is located on the back of the left thigh; and the fourth transducer 24A is located on the front of the right thigh. As to pairs, the first transducer 21A and the second transducer 22A may form a first pair of transducers, and the third transducer 23A and the fourth transducer 24A may form a second pair of transducers. In other embodiments, more than two pairs of transducers may be used for applying TTFields to the subject's body.

Figure 3A:
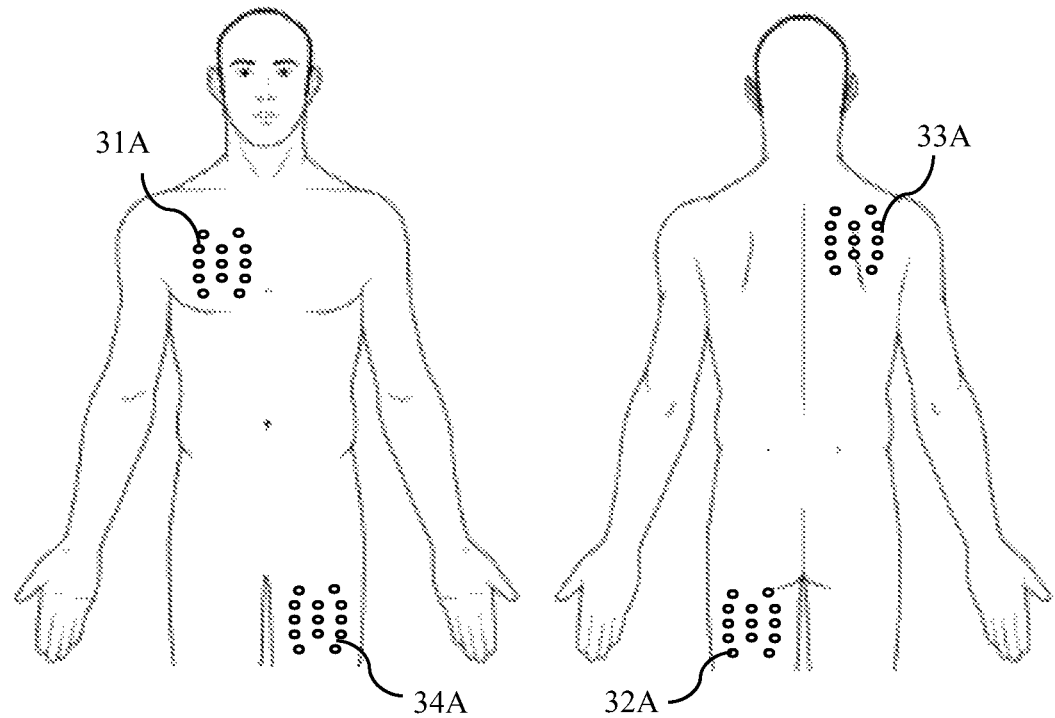
FIGS. 3A-3E depict examples of transducer layouts with two pairs of transducers.

FIGS. 3A-3E depict examples of transducer layouts with two pairs of transducers for applying TTFields to the subject's torso. In FIG. 3A, the first transducer 31A is located on the front of the right thorax, the second transducer 32A is located on the back of the left thigh, the third transducer 33A is located on the back of the right thorax, and the fourth transducer 34A is located on the front of the left thigh. The first and second transducers 31A and 32A may form a first pair of transducers, and the third and fourth transducers 33A and 34A may form a second pair of transducers. In another example, the first and fourth transducers 31A and 34A may form a first pair of transducers, and the third and second transducers 33A and 32A may form a second pair of transducers.

Figure 3B:
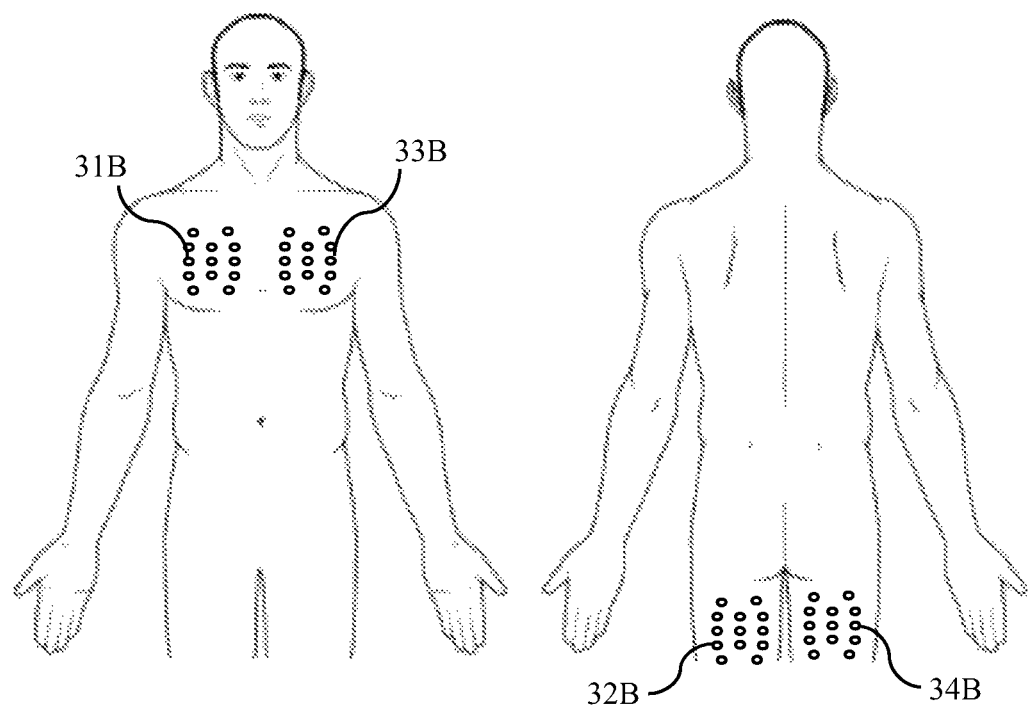

In FIG. 3B, the first transducer 31B is located on the front of the right thorax, the second transducer 32B is located on the back of the left thigh, the third transducer 33B is located on the front of the left thorax, and the fourth transducer 34B is located on the back of the right thigh. The first and second transducers 31B and 32B may form a first pair of transducers, and the third and fourth transducers 33B and 34B may form a second pair of transducers.

Figure 3C:
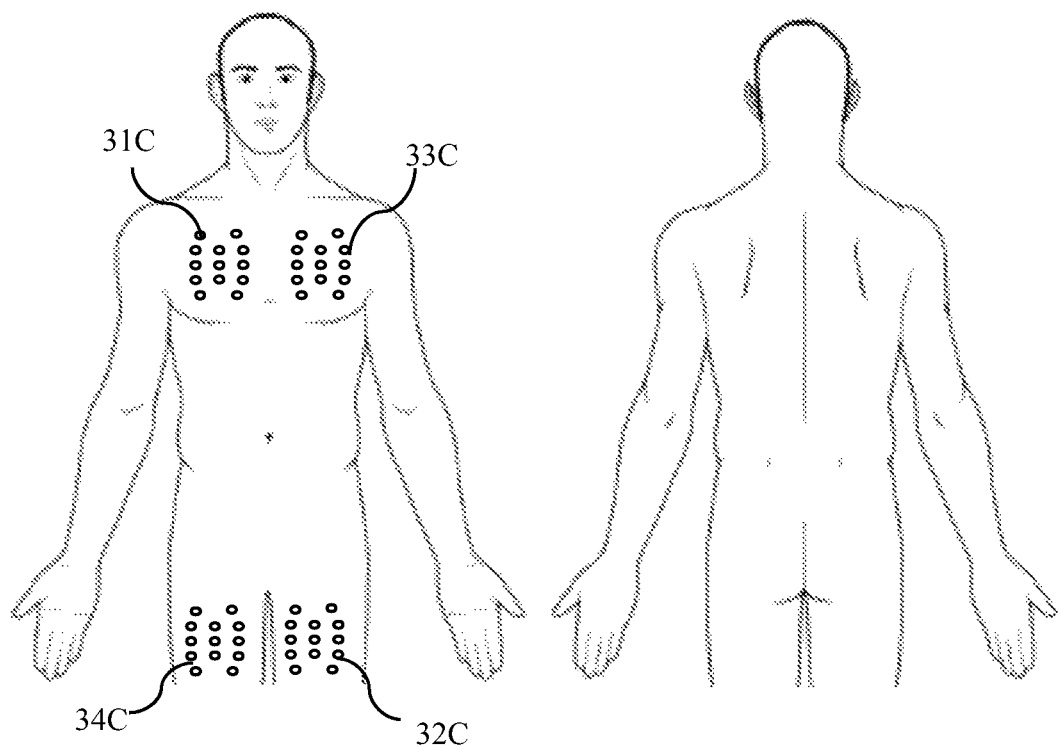

In FIG. 3C, the first transducer 31C is located on the front of the right thorax, the second transducer 32C is located on the front of the left thigh, the third transducer 33C is located on the front of the left thorax, and the fourth transducer 34C is located on the front of the right thigh. The first and second transducers 31C and 32C may form a first pair of transducers, and the third and fourth transducers 33C and 34C may form a second pair of transducers.

Figure 3D:
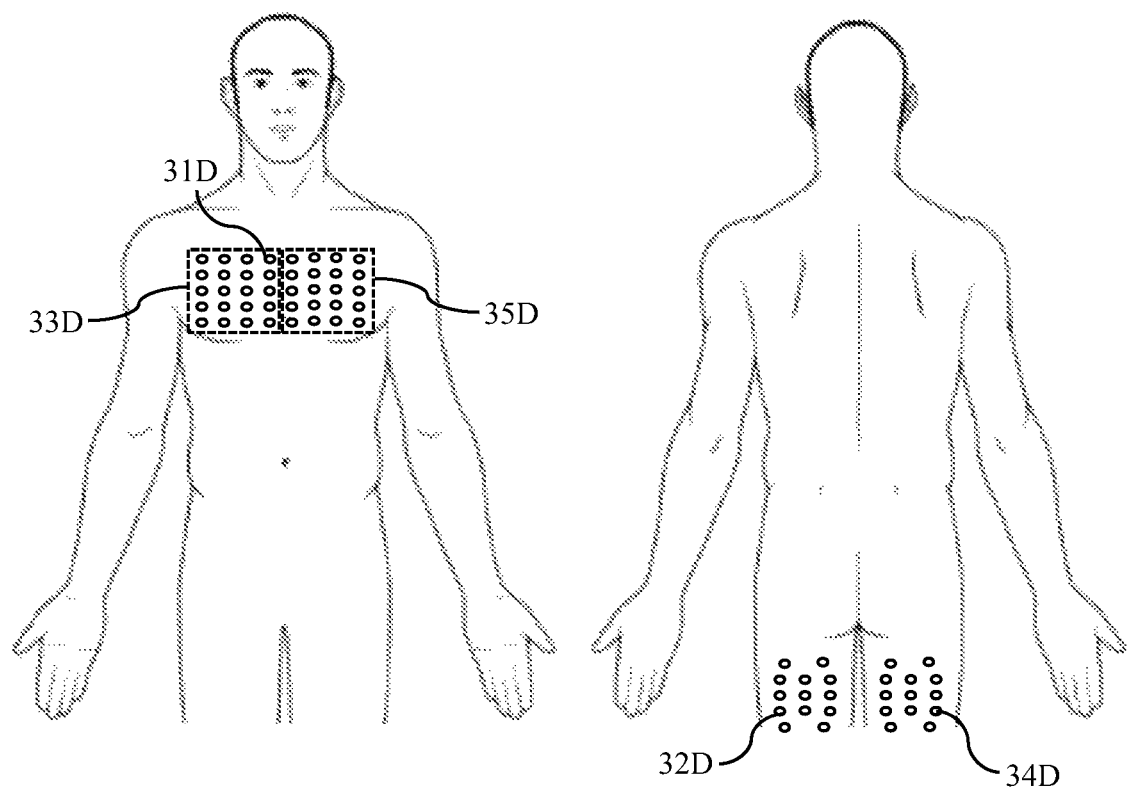

In FIG. 3D, the first transducer 31D is located on the front of the thorax, and the second transducer 32D and the fourth transducer 34D are located on the back of the left thigh and on the back of the right thigh, respectively. A first part 33D of the first transducer 31D and the second transducer 32D may form a first pair of transducers, and a second part 35D of the first transducer 31D and the fourth transducer 34D may form a second pair of transducers. In one example, the first part of the first transducer 33D does not overlap with the second part of the first transducer 35D. In another example, the first part of the first transducer 33D may partially overlap with the second part of the first transducer 35D.

Figure 3E:
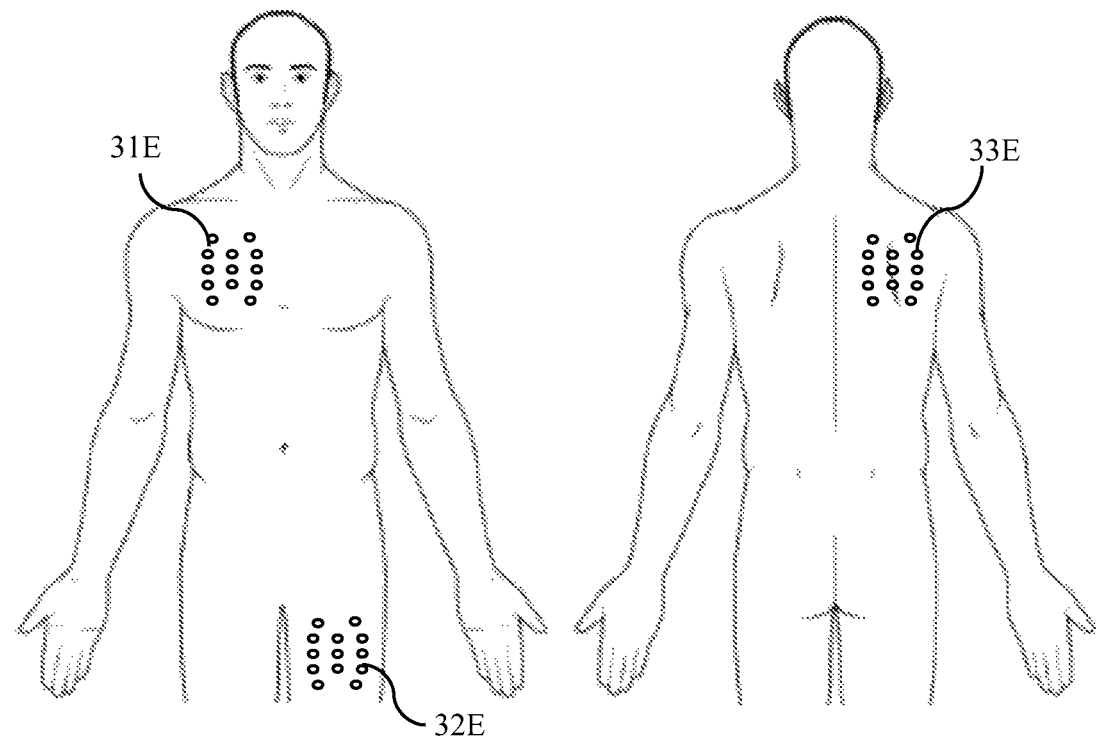

In FIG. 3E, the first transducer 31E is located on the front of the right thorax, the third transducer 33E is located on the back of the right thorax, and the second transducer 32E is located on the front of the left thigh. The first and second transducers 31E and 32E may form a first pair of transducers, and the third and second transducers 33E and 32E may form a second pair of transducers.

Figure 4A:
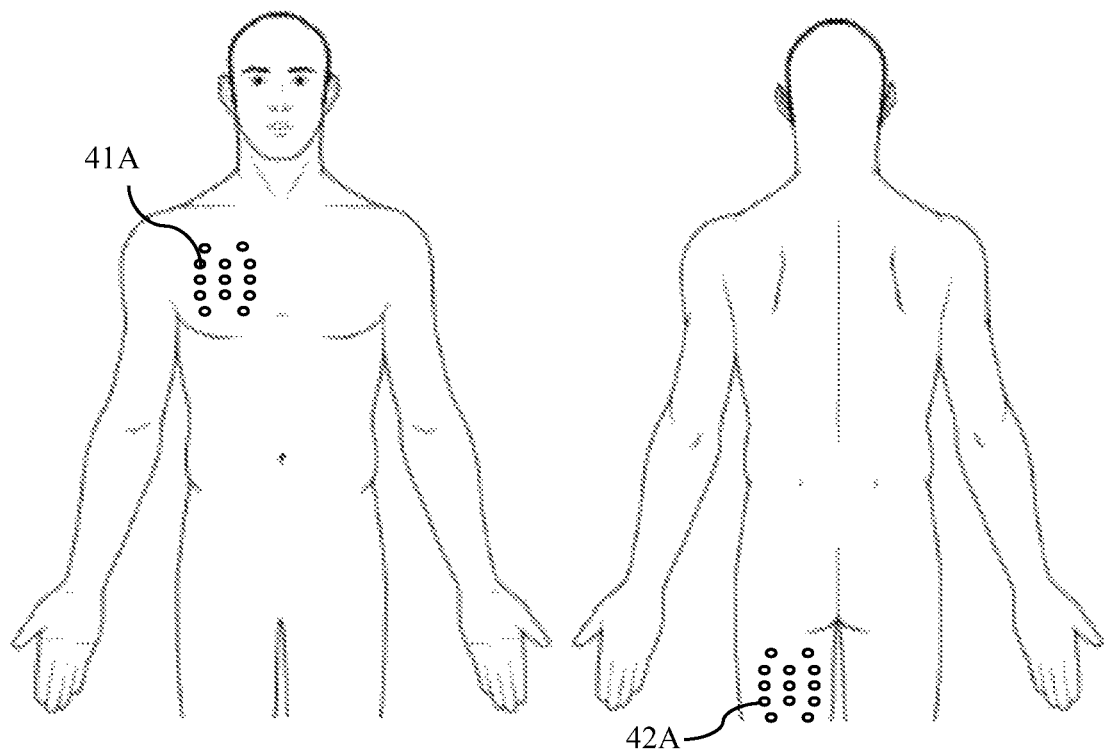
Figure 4B:
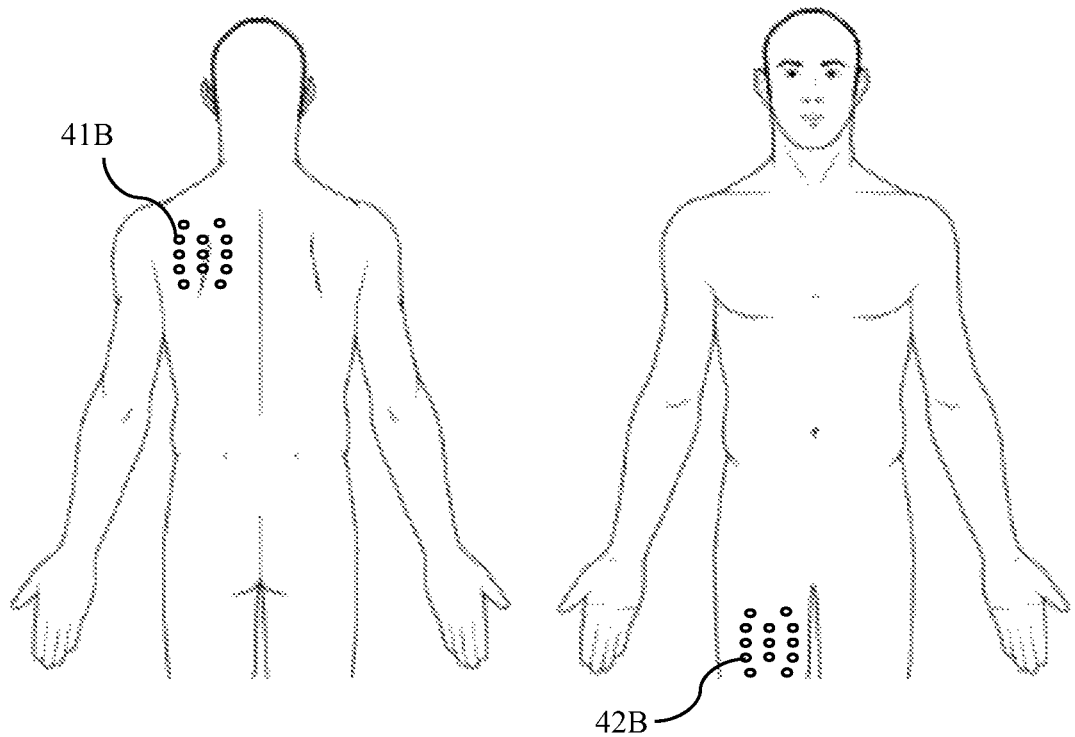

FIGS. 4A-4E depict examples of transducer layouts with one pair of transducers for applying TTFields to the torso of the subject's body. Various combinations of these pairs of transducers or similar pairs of transducers may be used together. In FIG. 4A, the first transducer 41A is located on the front of the right thorax, and the second transducer 42A is located on the back of the left thigh. In FIG. 4B, the first transducer 41B is located on the back of the left thorax, and the second transducer 42B is located on the front of the right thigh. In FIG. 4C, the first transducer 41C is located on the back of the right thorax, and the second transducer 42C is located on the front of the left thigh. In FIG. 4D, the first transducer 41D is located below the left armpit, and the second transducer 42D is located on the outer side of the right thigh. Instead of the outer side of the thigh, the transducer may be located on the inner side of the thigh. In FIG. 4E, the first transducer 41E is located on the front of the right thorax, and the second transducer 42E is located on the front of the left thigh.

The locations of the transducers that are located below the torso may be flexible. For example, where a pair of transducers includes a first transducer located on the torso and a second transducer located below the torso, the location of the second transducer may be anywhere on the thigh of the subject's body (e.g., on a front, back, outer side, or inner side of a thigh, a combination thereof, or a partially or fully overlapping combination thereof).

Various combinations of pairs of transducers as discussed herein, or similar pairs of transducers, may be used together. Various locations of transducers, such as those discussed herein or in other locations, may be used. A transducer may be used in a single pair of transducers or in two or more pairs of transducers. A transducer may be partitioned to be used in a single pair of transducers or in two or more pairs of transducers. The transducers, the transducer locations, the pairs of transducers, and the two or more pairs of transducers discussed herein are not exhaustive.

Figure 5A:
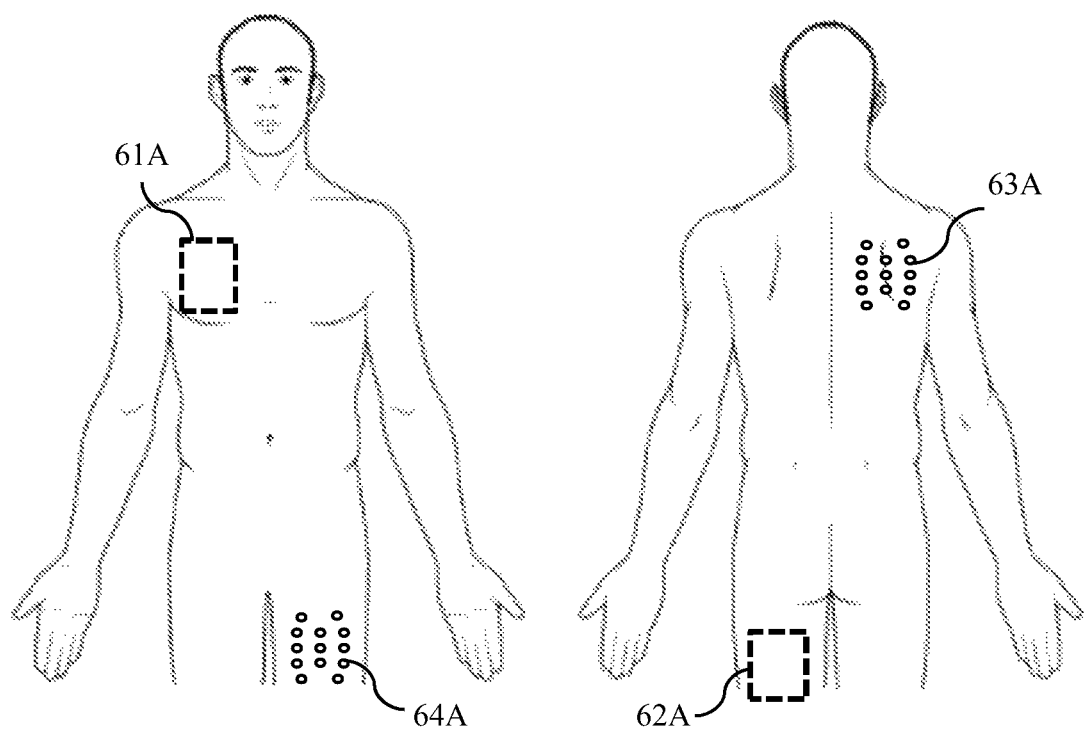
FIGS. 5A and 5B depict examples of re-locating the transducers on the torso.
Figure 5B:
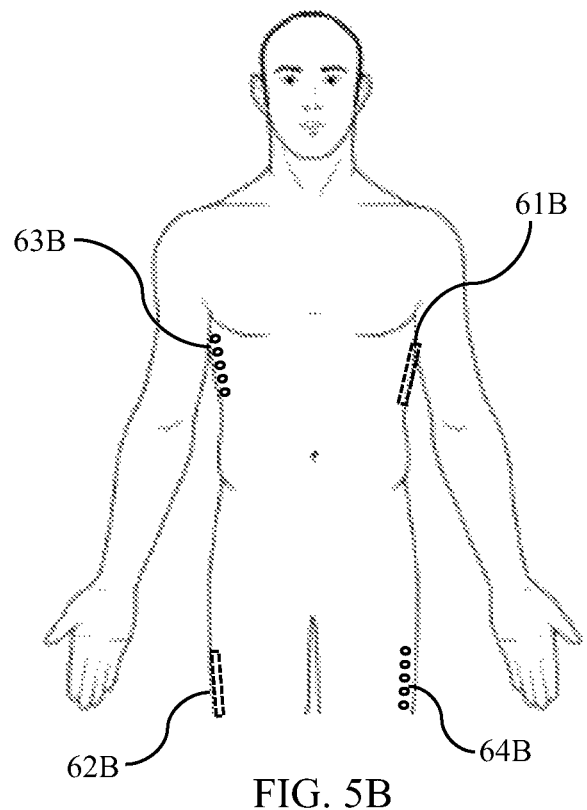

FIGS. 5A and 5B depict examples of re-locating the transducers on the torso of the subject's body. In the example depicted in FIG. 5A, the first transducer was located at the first location 61A and re-located at the third location 63A. The second transducer was located at the second location 62A and re-located at the fourth location 64A. The first location 61A is on the front of the right thorax, the third location 63A is on the back of the right thorax, the second location 62A is the back of the left thigh, and the fourth location 64A is the front of the left thigh.

In the example depicted in FIG. 5B, the first transducer was located at the first location 61B and re-located at the third location 63B. The second transducer was located at the second location 62B and re-located at the fourth location 64B. The first location 61B is below the left armpit, the third location 63B is below the right armpit, the second location 62B is on the outer side of the right thigh, and the fourth location 64B is on the outer side of the left thigh.

When re-locating transducers according to steps S502 and S504 of FIG. 1, the transducers may be re-located to different areas of the subject's body than those illustrated in the examples of FIGS. 5A and 5B. The transducers may be re-located to areas of the subject's body to deliver a similar or complementary amount of TTFields.

Figure 6A:
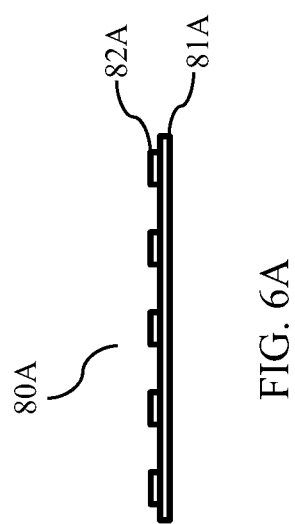
FIGS. 6A and 6B depict examples of the structure of the transducers.
Figure 6B:
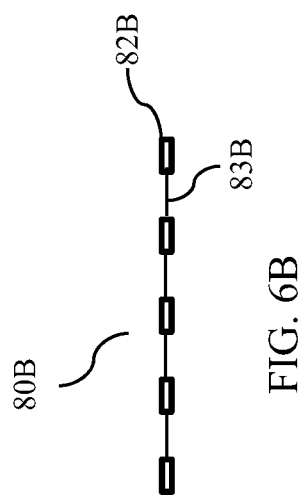

The structure of the transducers may take many forms. The transducers may be affixed to the subject's body or attached to or incorporated in clothing covering the subject's body. In FIG. 6A, the transducer 80A has a substrate 81A and a plurality of electrode elements 82A positioned on the substrate 81A. The substrate 81A is configured for attaching the transducer 80A to a subject's body. Suitable materials for the substrate 81A include, for example, cloth, foam, flexible plastic, and/or a conductive medical gel. The substrate 81A may be a layer of conducting medical gel with a minimum thickness of 0.5 mm. In this situation, the transducer 80A is affixed to the subject's body via the substrate 81A. The transducer may be conductive or non-conductive. FIG. 6B depicts another example of the structure of the transducer 80B. In this example, the transducer 80B includes a plurality of electrode elements 82B that are electrically and mechanically connected to one another without a substrate. In one example, the electrode elements 82B are connected to each other through conductive wires 83B.

The transducer may include any desired number of electrode elements 82A, 82B. Various shapes, sizes, and materials may be used for the electrode elements 82A, 82B. Any constructions for implementing the transducer (or electric field generating device) for use with embodiments of the invention may be used, as long as they are capable of (a) delivering TTFields to the subject's body and (b) being positioned at the locations specified herein.

Figure 7:
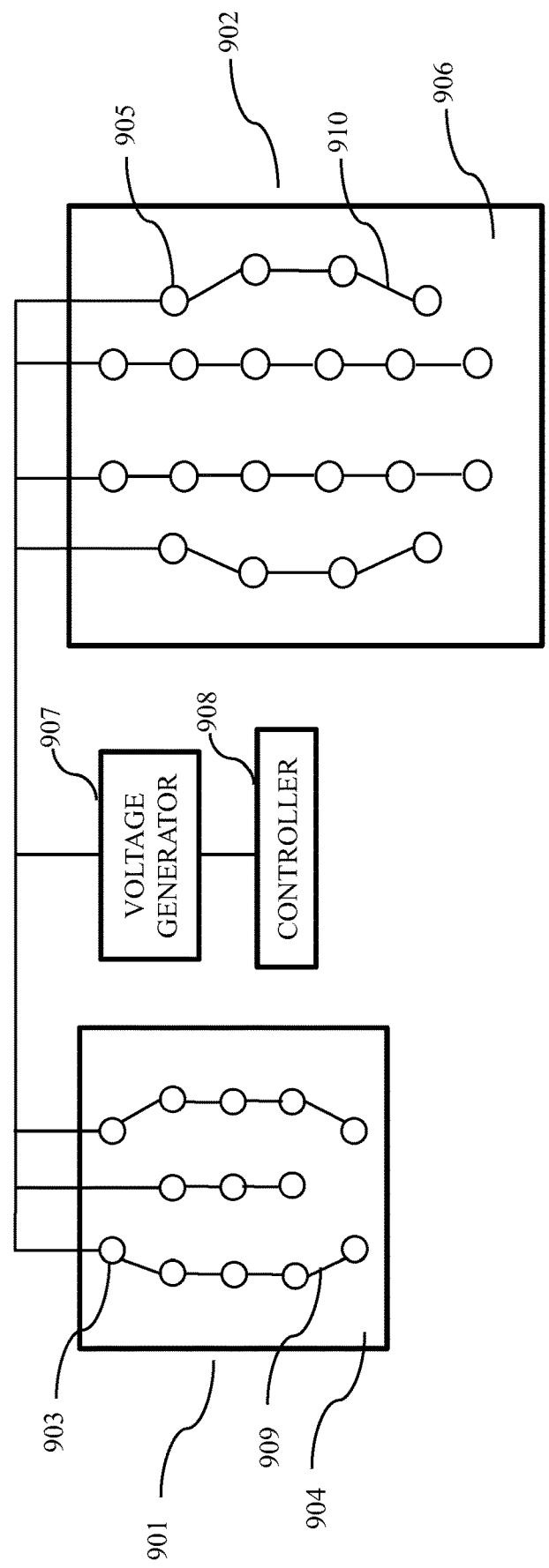
FIG. 7 depicts one example of a configuration of one pair of transducers.

FIG. 7 depicts one example of the configuration of one pair of transducers. In this example, the first transducer 901 includes 13 electrode elements 903 which are positioned on the substrate 904 and electrically and mechanically connected to one another through a conductive wiring 909. Similarly, the second transducer 902 includes 20 electrode elements 905 which are positioned on the substrate 906 and electrically and mechanically connected to one another through a conductive wiring 910. The first transducer 901 and the second transducer 902 are connected to an AC voltage generator 907 and a controller 908. The controller 908 may include one or more processors and memory accessible by the one or more processors. The memory may store instructions that when executed by the one or more processors control the AC voltage generator 907 to implement one or more embodiments of the invention (e.g., by providing a first voltage to the first transducer and a second voltage to the second transducer).

Figure 8:
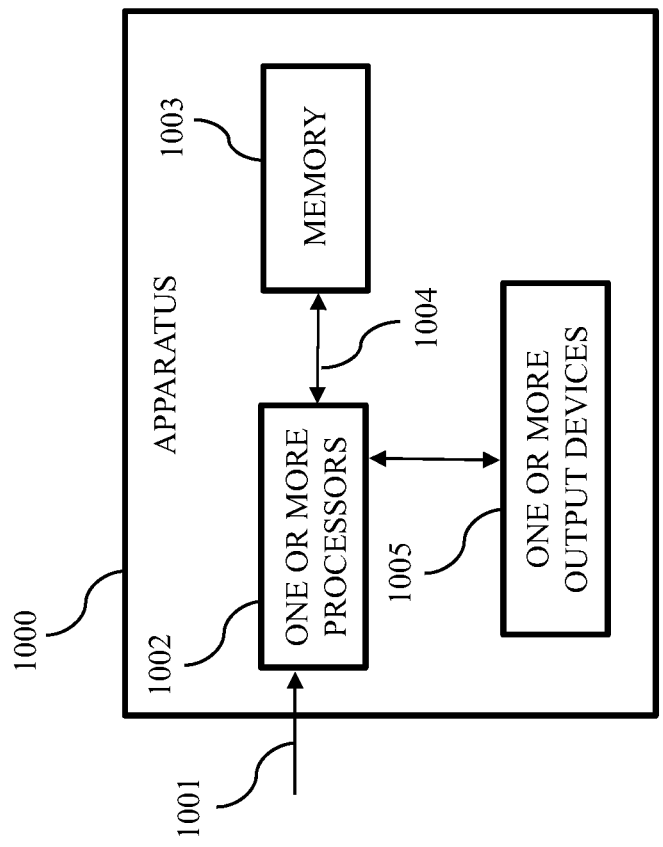
FIG. 8 depicts one example of an apparatus to determine locations of transducers on a subject's body for applying TTFields.

FIG. 8 depicts an exemplary apparatus to determine locations of transducers for applying TTFields. In this example, the apparatus 1000 includes one or more processors 1002, one or more output devices 1005, and a memory 1003. The memory 1003 is accessible by the one or more processors 1002 via a link 1004 so the one or more processors 1002 can read information from and write information to the memory 1003. In one example, based on user input 1001, the one or more processors 1002 generate simulation results of a plurality of locations for attaching transducers, rank the plurality of locations, and make one or more recommendations to a user based on the ranking, which are output on the output devices 1005. In another example, the user may give feedback regarding the one or more recommendations through the output devices 1005, and the one or more processors 1002 may generate different recommendations based on the feedback.

Figure 9:
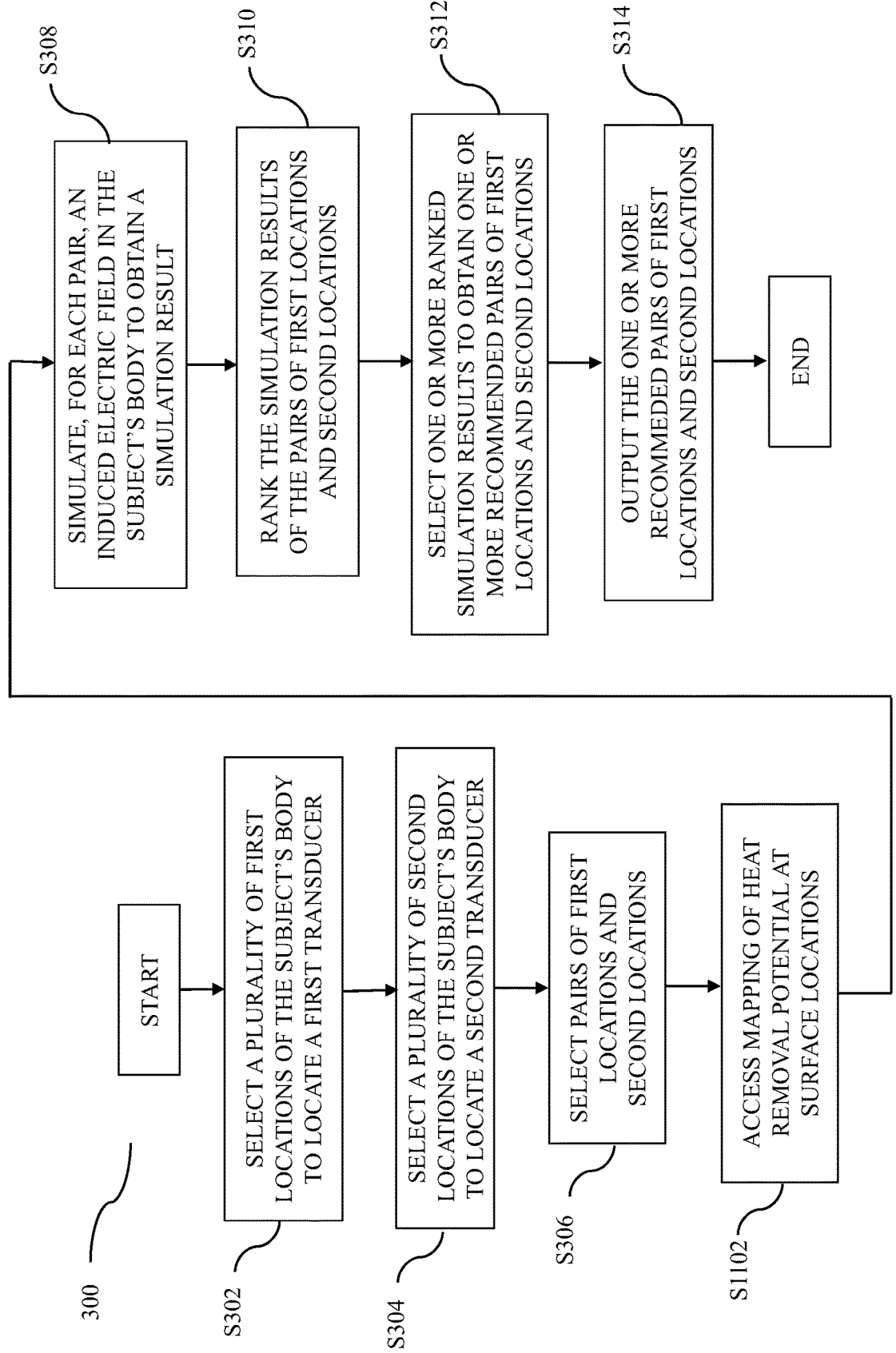
FIG. 9 is a flowchart depicting an example of determining locations of transducers on a subject's body for applying TTFields.

FIG. 9 is a flowchart describing an example method 300 for determining locations of transducers on a subject's body for applying TTFields. In FIG. 9, at step S302, a plurality of first locations of the subject's body are selected to locate a first transducer, wherein the plurality of first locations are on the torso of the subject's body. At step S304, a plurality of second locations of the subject's body are selected to locate a second transducer, wherein the plurality of second locations are below the torso of the subject's body. Below the torso of the subject's body may include, for example, on the thigh of the subject's body. At step S306, pairs of first locations and second locations are selected. Each pair has one first location selected from the plurality of first locations and one second location selected from the plurality of second locations, and each pair has a different combination of first and second locations.

In some embodiments, the method 300 may incorporate a measure of heat removal potential of a subject's body to determine locations of transducers on the subject's body for applying TTFields. At step S1102, the method 300 may include accessing a mapping of heat removal potential at surface locations corresponding to surface locations of the subject's body. For example, step S1102 may include accessing a mapping of the subject's body indicating a heat removal potential at multiple surface locations of the subject's body, as discussed below.

At step S308, simulation results for an induced electric field in the torso of the subject's body are generated. Generating simulation results may include, for example: obtaining a three-dimensional model of AC electrical conductivity of the relevant anatomic volume; identifying the volume targeted for treatment within the three-dimensional model; automatically placing transducers on the three-dimensional model and setting relevant boundary conditions for the three-dimensional model; and calculating the electric field that develops within the model (e.g., using a Finite Element method analysis) once transducers have been placed on the model and boundary conditions applied. In an embodiment, for each pair, the induced electric field in the torso of the subject's body is simulated based at least partially on the mapping of heat removal potential accessed at step S1102 to obtain the simulation results.

At step S310, based on the simulation results, a ranking of the simulations results of each pair of locations is generated. This may involve, for example, running an optimization algorithm to find the layout that yields optimal electric field distributions within the target volume. The simulation results may be ranked in order of maximized electric field within the diseased regions of the subject's body. At step S312, based on the ranked simulations results, one or more recommendations of the pairs of first locations and second locations are generated. In an embodiment, the one or more ranked simulation results are selected based at least partially on the mapping of heat removal potential accessed at step S1102. At step S314, the one or more recommended pairs of first locations and second locations are output to the user.

Figure 10:
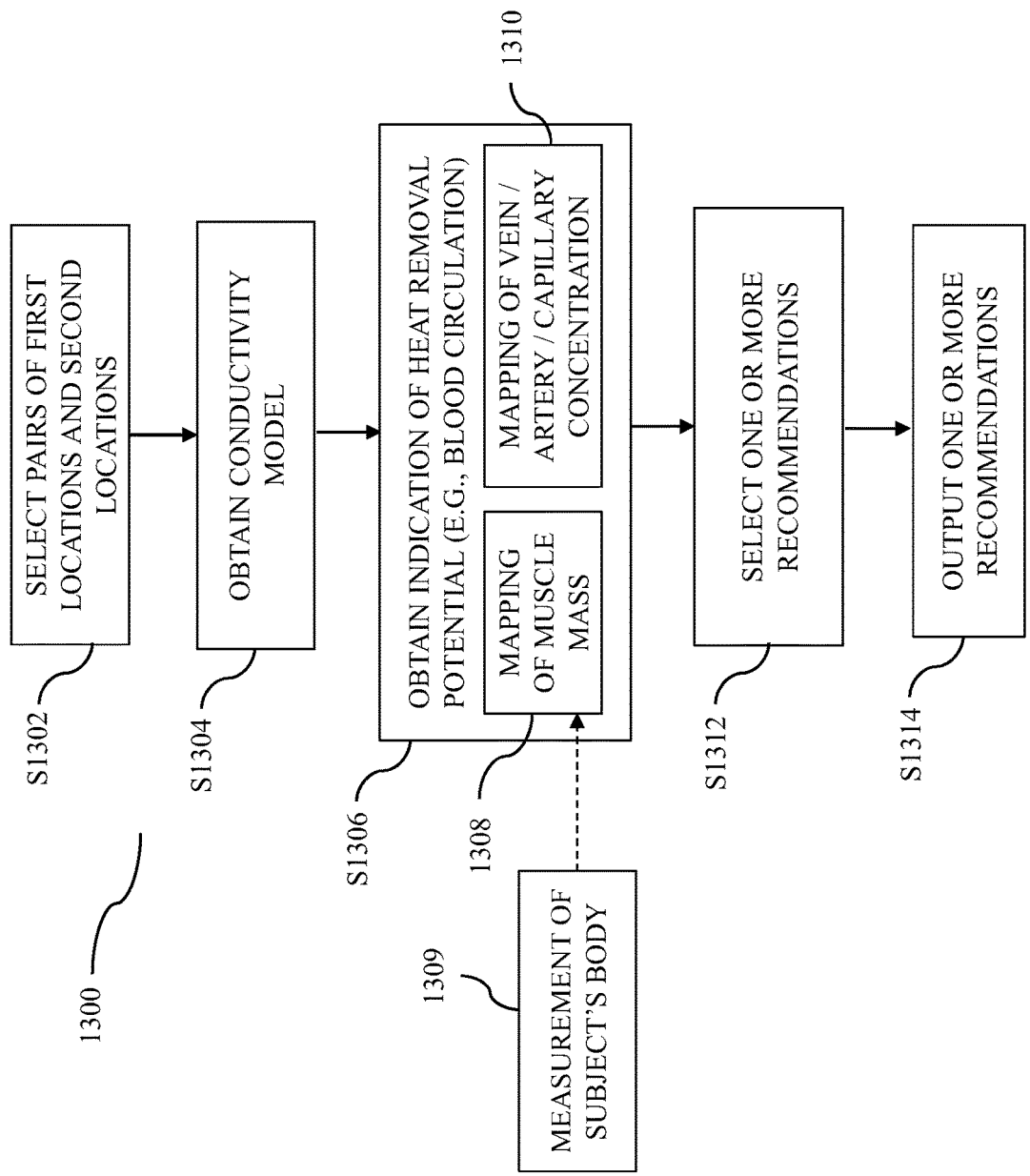
FIG. 10 is a flowchart depicting another example of determining locations of transducers on a subject's body for applying TTFields.

FIG. 10 is a flowchart describing an example computer-implemented method for determining locations of transducers on a subject's body for applying TTFields. The computer comprises one or more processors and a memory accessible by the one or more processors, the memory storing instructions that when executed by the one or more processors cause the computer to perform the method 1300.

With reference to FIG. 10, at step S1302, pairs of first locations and second locations are selected, each pair of locations having a first location to locate a first transducer and a second location to locate a second transducer. Each pair may have one first location selected from a plurality of first locations and one second location selected from a plurality of second locations. Each pair may have a different combination of first locations and second locations. One or more of the pairs of locations may include at least one location on the subject's torso.

At step S1304, a three-dimensional model of AC electrical conductivity (e.g., at the frequency that will be used for the TTFields treatment) of the relevant anatomic volume is obtained using any of a variety of approaches that will be apparent to persons skilled in the relevant arts. This three-dimensional model specifies the conductivity of each voxel.

At step S1306, the method 1300 comprises obtaining, for each location in the plurality of pairs of locations on the subject's body, an indication of heat removal potential at a surface of the subject's body. The indication of heat removal potential at the surface of the subject's body may be proportional to an amount of blood circulation proximate the surface at the location of the subject's body.

In an example, the indication of heat removal potential at the surface of the subject's body may be proportional to an amount of muscle mass at the location of the subject's body. Even though muscle movement generates heat, areas of high muscle mass in a subject's body are generally more effective than areas of low muscle mass at moving heat away from the surface of the body due to increased blood circulation through the muscle. In some embodiments, the indication of heat removal potential at the surface of the subject's body may relate to an amount of sweat expected at the location of the subject's body, an amount of glandular tissue at the location, or whether clothing is expected to cover the location.

The method at step S1306 may include accessing a mapping 1308 of relative muscle mass at surface locations of the subject's body; and obtaining, for each location in the plurality of pairs of locations on the subject's body, the amount of muscle mass at the location of the subject's body from the mapping 1308. The mapping may be a model of a human body including at least one portion of the body divided into a plurality of zones on the surface of the at least one portion of the body, and a relative muscle mass value corresponding to each zone. In an embodiment, the mapping 1308 is selected from one or more predetermined models of muscle mass distribution in humans. For example, the mapping 1308 may be: a standard mapping of relative muscle mass used for all human subjects; selected from a group of two standard mappings (for male subjects and female subjects) of relative muscle mass; or selected from a finite number of mappings of relative muscle mass in response to one or more user inputs such as, for example, sex, height, and weight. In an embodiment, the mapping 1308 of relative muscle mass is generated for an individual subject based on an input of at least one measurement 1309 of the subject's body. Such measurements 1309 may include a height, weight, circumferential measurements of one or more of the subject's body parts (e.g., chest, waist, hips, forearm, wrist, neck, etc.), grip strength measurement, caliper measurement, or image data, among others.

In an example, the indication of heat removal potential at the surface of the subject's body may be proportional to a concentration of at least one of veins, arteries, or capillaries proximate the surface at the location of the subject's body. This relationship takes advantage of vascular changes that occur in a subject's body, such as constriction or enlargement of vessels in response to temperature changes (e.g., blood vessels expanding to remove heat from the area). Areas of the subject's body having more veins, arteries, and/or capillaries close to the surface may provide greater heat removal potential.

The method at step S1306 may include accessing a mapping 1310 of at least one of veins, arteries, or capillaries proximate surface locations of the subject's body; and obtaining, for each location in the plurality of pairs of locations on the subject's body, the concentration of at least one of veins, arteries, or capillaries proximate the surface at the location of the subject's body from the mapping 1310. The mapping 1310 may be a model of a human body including at least one portion of the body divided into a plurality of zones each representing part of the surface of the at least one portion of the body, and a concentration of at least one of veins, arteries, or capillaries proximate the surface corresponding to each zone. In an embodiment, the mapping 1310 is selected from one or more predetermined models representing a typical circulatory system in humans. The mapping 1310 may be: a standard mapping of concentrations of veins, arteries, and/or capillaries used for all human subjects; selected from a group of two standard mappings (for male subjects and female subjects) of a circulatory system; or generated based on image data for the subject.

At step S1312, the method 1300 comprises selecting one or more recommended pairs of first locations and second locations. At step 1312, the one or more recommended pairs are selected based at least on the model of AC electrical conductivity of S1304 and the indication of heat removal potential of S1306 for each location. Since the one or more recommend pairs are selected based on the indication of heat removal potential of S1306, the one or more recommended pairs may include a location having a relatively high muscle mass, a high concentration of veins, arteries, and/or capillaries, and/or other markers of increased circulation. The one or more recommended pairs may comprise a location in a region of a torso of the subject. The one or more recommended pairs may comprise a location in a region of a shoulder, thigh, or thorax of the subject. At step S1314, the method 1300 comprises outputting (e.g., to a user) the one or more recommended pairs of first locations and second locations.

FIG. 11 is a flowchart depicting an example method of performing step S1312 of FIG. 10. At step S1400, the method may comprise simulating, for each pair of locations, an induced electric field in the portion of the subject's body between the first transducer and the second transducer of each pair, based on the model of AC electrical conductivity (S1304 of FIG. 10) and the indication of heat removal potential (S1306 of FIG. 10) at the surface of the subject's body for the locations of each pair. The indication of heat removal potential may be input to simulation software to generate the results. The heat removal potential at the pair locations may affect an amount of energy output via the transducers, since higher heat removal potential enables a subject's body to remove heat caused by transducers operating at higher power levels. The simulation may involve applying a weighting factor to transducer locations based on their heat removal potential. At step S1402, the method may comprise ranking simulation results of the pairs of first locations and second locations. At step S1404, the method may comprise selecting one or more ranked simulation results as the one or more recommended location pairs.

FIG. 12 is a flowchart depicting another example method of performing step S1312 of FIG. 10. At step S1500, the method may comprise simulating, for each pair of locations, an induced electric field in the portion of the subject's body between the first transducer and the second transducer of each pair based on the model of AC electrical conductivity (S1304 of FIG. 10). At step S1502, the method may comprise ranking the simulation results of the pairs of first locations and second locations. At step S1504, the method may comprise selecting two or more potential pairs of first locations and second locations based on the ranked simulation results. At step S1506, the method may comprise comparing the indication of heat removal potential (S1306 of FIG. 10) at the surface of the subject's body for locations of the two or more potential pairs. At step S1508, the method may comprise selecting one or more potential pairs having a highest indication of heat removal potential as the one or more recommended pairs of first locations and second locations. As such, the method of FIG. 12 involves using the indication of heat removal potential for various surface locations on the subject's body to break a tie between a plurality of transducer location pairs that according to the simulation results would yield substantially similar electric field deliveries to the target region.

Table 1 shows simulation results for Sample Nos. 1-8 based on step S308 in FIG. 9. Each transducer layout of Sample Nos. 1-8 includes one pair of transducers (a first transducer and a second transducer). Each transducer in Sample Nos. 1-3, 5, 7, and 8 include 13 electrode elements, and each transducer in Sample Nos. 4 and 6 include 20 electrode elements. All of the field intensities depicted herein were generated by running simulations at 150 kHz using a DUKE model by ZMT (Zurich), a highly detailed computational human male phantom. The simulations were performed using the low frequency solver of the Sim4Life software package, which uses a Finite Differences Method to solve the model. Consequently, discretization is performed by dividing the model into voxels (voxelization). To optimize accuracy with calculation speed, the model was voxelized with a maximum resolution of 0.625 mm around the disks. In one example, the resolution within the body was between 1 and 2 mm. To simulate delivery of TTFields using the NovoTTF-100L(P), Dirichlet conditions (e.g., constant voltage at a frequency of 150 kHz) were applied to the outer faces of the disks of the transducers. All disks within one pair of transducers were set to the same voltage level. The difference in voltage between the two transducers within the pair was set so that the average current per-disk was 200 mA peak to peak, which resulted in the total current of 2.6 A peak to peak for transducers with 13 disks and 4 A peak to peak for transducers with 20 disks.

For each of Samples 1-8, the numbers of electrode elements in each transducer and the locations of each transducer on the subject's body (and a representative figure) are provided in Table 1. The simulation results are also provided in Table 1. The simulation results include a mean electric field intensity in the torso and a percentage of the torso volume that received an intensity above 1 V/cm.

TABLE 1

Simulation results of a plurality of transducer layouts.

| Sample No. | 1st transducer location | No. of electrode elements for 1st transducer | 2nd transducer location | No. of electrode elements for 2nd transducer | Illustrative Figure | Mean field intensity (V/cm) | % volume above 1 V/cm |
|---|---|---|---|---|---|---|---|
| 1 | Front right thorax | 13 | Back left thigh | 13 | FIG. 4A | 1.16 | 54.54 |
| 2 | Front left thorax | 13 | Back right thigh | 13 | FIG. 3B, transducers 33B and 34B | 1.09 | 51.81 |
| 3 | Back left thorax | 13 | Front right thigh | 13 | FIG. 4B | 1.08 | 53.36 |
| 4 | Back left thorax | 20 | Front right thigh | 20 | FIG. 4B | 1.65 | 81.18 |
| 5 | Back right thorax | 13 | Front left thigh | 13 | FIG. 4C | 1.12 | 56.89 |
| 6 | Back right thorax | 20 | Front left thigh | 20 | FIG. 4C | 1.70 | 84.16 |
| 7 | Left armpit | 13 | Outer right thigh | 13 | FIG. 4D | 0.86 | 35.79 |
| 8 | Right armpit | 13 | Outer left thigh | 13 | FIG. 6B, transducers 63B and 64B | 0.93 | 37.18 |

From the simulation results of Sample Nos. 1 to 6, the torso of the subject's body has an average electric field intensity of at least 1.0 V/cm, and at least 50% of volume of the torso of the subject's body has electric field intensities of at least 1.0 V/cm. From the simulation results of Sample Nos. 4 and 6, the torso of the subject's body has an average electric field intensity of at least 1.6 V/cm, and at least 80% of volume of the torso of the subject's body has electric field intensities of at least 1.0 V/cm. For Samples 1, 2, 3, and 5, the simulation results show that placing the transducers in the front or in the back of the thorax does not significantly influence the mean electric field intensity and the percentage of torso volume that received an intensity above 1 V/cm. As such, the locations of the transducers may be selected based on comfort level and convenience without compromising the treatment effects of the TTFields.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

The invention claimed is:

1. A method of applying tumor treating fields to a torso of a subject's body, the method comprising:
    locating a first transducer at a first location of the subject's body, the first location being on the torso of the subject's body;
    locating a second transducer at a second location of the subject's body, the second location being below the torso of the subject's body; and
    inducing an electric field between at least part of the first transducer and at least part of the second transducer,
    wherein the first location is on a thorax of the subject's body, and the second location is on a thigh of the subject's body.

2. The method of claim 1, wherein the first location is on a front of the thorax of the subject's body, and the second location is on a back or an outer side of the thigh of the subject's body, or
    wherein the first location is on a back of the thorax of the subject's body, and the second location is on a front or an outer side of the thigh of the subject's body.

3. The method of claim 1, wherein the first location is on a left side of the thorax of the subject's body, and the second location is on a right thigh of the subject's body, or wherein the first location is on a right side of the thorax of the subject's body, and the second location is on a left thigh of the subject's body.

4. The method of claim 1, wherein the first location is on a front or a back of the thorax of the subject's body and not below an armpit of the subject's body.

5. The method of claim 1, further comprising:
    after inducing the electric field for more than a first time period,
        ceasing the electric field;
        re-locating the first transducer at a third location of the subject's body, the third location being on the torso of the subject's body and not overlapping with the first location;
        re-locating the second transducer at a fourth location of the subject's body, the fourth location being below the torso of the subject's body and not overlapping with the second location; and
        inducing another electric field between at least part of the first transducer and at least part of the second transducer.

6. The method of claim 1, further comprising:
    locating a third transducer at a third location of the subject's body, the third location being on the torso of the subject's body and not overlapping with the first location;
    locating a fourth transducer at a fourth location of the subject's body, the fourth location being below the torso of the subject's body and not overlapping with the second location; and
    alternately inducing the electric field between at least part of the first transducer and at least part of the second transducer and inducing another electric field between at least part of the third transducer and at least part of the fourth transducer.

7. The method of claim 1, wherein when the electric field is induced, at least 50% of volume of the torso of the subject's body has electric field intensities of at least 1.0 V/cm.

8. The method of claim 1, wherein when the electric field is induced, the torso of the subject's body has an average electric field intensity of at least 1.0 V/cm.

9. The method of claim 1, wherein the electric field is induced in a thorax of the subject's body and an abdomen of the subject's body.

* * * * *